(12) United States Patent
Clozel et al.

(10) Patent No.: US 8,541,433 B2
(45) Date of Patent: Sep. 24, 2013

(54) COMBINATION COMPRISING MACITENTAN AND PACLITAXEL FOR TREATING MULTI-DRUG RESISTANT OVARIAN CANCER

(75) Inventors: Martine Clozel, Binningen (CH); Urs Regenass, Allschwil (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 104 days.

(21) Appl. No.: 12/867,939

(22) PCT Filed: Feb. 19, 2009

(86) PCT No.: PCT/IB2009/050677
§ 371 (c)(1),
(2), (4) Date: Aug. 17, 2010

(87) PCT Pub. No.: WO2009/104149
PCT Pub. Date: Aug. 27, 2009

(65) Prior Publication Data
US 2010/0311774 A1    Dec. 9, 2010

(30) Foreign Application Priority Data
Feb. 20, 2008   (WO) .................. PCT/IB2008/050607

(51) Int. Cl.
*A61K 31/515* (2006.01)
*A61K 31/505* (2006.01)
*C07D 403/00* (2006.01)

(52) U.S. Cl.
USPC ........... 514/274; 514/269; 514/256; 514/247; 544/296; 544/295; 544/242; 544/224

(58) Field of Classification Search
None
See application file for complete search history.

(56) References Cited

U.S. PATENT DOCUMENTS

| | | | |
|---|---|---|---|
| 5,504,102 A * | 4/1996 | Agharkar et al. | 514/449 |
| 7,094,781 B2 * | 8/2006 | Bolli et al. | 514/235.8 |
| 8,268,847 B2 | 9/2012 | Clozel et al. | |
| 2004/0121971 A1 | 6/2004 | Chen et al. | |
| 2008/0233188 A1 | 9/2008 | Adesuyi et al. | |
| 2010/0004274 A1 | 1/2010 | Adesuyi et al. | |

FOREIGN PATENT DOCUMENTS

| | | |
|---|---|---|
| WO | WO 02/053557 | 7/2002 |
| WO | WO 2004/037235 | 5/2004 |
| WO | WO 2006/056760 | 6/2006 |
| WO | WO 2007/031933 | 3/2007 |

OTHER PUBLICATIONS

"Exploratory Phase III Study of Paclitaxel and Cisplatin Versus Paclitaxel and Carboplatin in Advanced Ovarian Cancer" by Neijt et al., J. Clin. Oncol. 18, 3084-92 (2000).*

Rosano, Laura, et al., "ZD4054, A Specific Antagonist of the Endothelin A Receptor, Inhibits Tumor Growth and Enhances Paclitaxel Activity in Human Ovarian Carcinoma In Vitro and In Vivo", Molecular Cancer Therapeutics, Jul. 2007, vol. 6, No. 7, pp. 2003-2011, XP002530275, ISSN: 1535-7163.
Adachi, M., et al., "Identification of a region of the human endothelin $ET_A$ receptor required for interaction with bosentan", European Journal of Pharmacology, Molecular Pharmacology Section, vol. 269, pp. 225-234, (1994).
Bagnato, A., et al., "Emerging role of the endothelin axis in ovarian tumor progression", Endocrine-Related Cancer, vol. 12, pp. 761-772, (2005).
Gould, P.L., "Salt Selection for Basic Drugs", International Journal of Pharmaceutics, vol. 33, pp. 201-217, (1986).
Hermann, E., et al., "The endothelin axis in urologic tumors: mechanisms of tumor biology and therapeutic implications", Expert Rev. Anticancer Ther., vol. 6(1), pp. 73-81, (2006).
Nelson, J., et al., "The endothelin axis: Emerging role in cancer", Nature Reviews Cancer, vol. 3, pp. 110-116, (2003).
Remington, The Science and Practice of Pharmacy, $21^{st}$ Edition (2005), Part 5, "Pharmaceutical Manufacturing" [published by Lippincott Williams & Wilkins].
Rosanó, L., et al., "Combined targeting of the endothelin A receptor and the epidermal growth factor receptor in ovarian cancer shows enhanced aniproliferative effects", American Association Cancer Research, Abstract No. 1509, (2007).
Rosanó, L., et al., "Endothelin-1-induced activation of the β-catenin pathway in human ovarian cancer cells is mediated through epidermal growth factor transactivation", American Association Cancer Research, Abstract No. 2772, (2006).
Rosanó, L., et al., "Endothelin-1 Induces Tumor Proteinase Activation and Invasiveness of Ovarian Carcinoma Cells", Cancer Research, vol. 61, pp. 8340-8346, (2001).
Rosanó, L., et al., "Endothelin-1 Promotes Epithelial-to-Mesenchymal Transition in Human Ovarian Cancer Cells", American Association Cancer Research, vol. 65(24), pp. 11649-11657, (2005).
Rosanó, L., et al., "Integrin-linked kinase functions as a downstream mediator of endothelin-1 to promote invasive behavior in ovarian carcinoma", Mol. Cancer Ther., vol. 5(4), pp. 833-842, (2006).

(Continued)

*Primary Examiner* — Brandon Fetterolf
*Assistant Examiner* — Theodore R West
(74) *Attorney, Agent, or Firm* — Hoxie & Associates LLC

(57) ABSTRACT

The invention relates to the combination of an endothelin receptor antagonist of formula (I) with paclitaxel, and in particular to this combination for therapeutic use, simultaneously, separately or over a period of time, in the treatment of ovarian cancer.

(I)

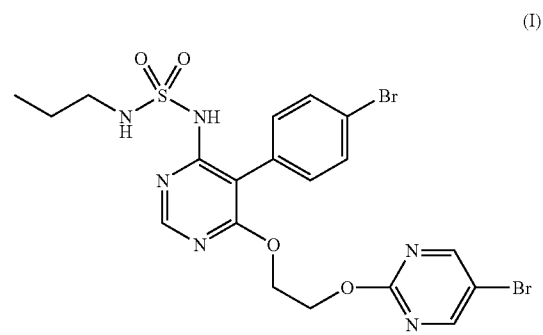

4 Claims, No Drawings

(56) References Cited

OTHER PUBLICATIONS

Rosanó, L., et al., "Therapeutic Targeting of the Endothelin A Receptor in Human Ovarian Carcinoma", Cancer Res., vol. 63, pp. 2447-2453, (2003).

Rosanó, L., et al., "ZD4054, a Potent Endothelin Receptor A Antagonist, Inhibits Ovarian Carcinoma Cell Proliferation", Experimental Biology and Medicine, vol. 231, pp. 1132-1135, (2006).

Spinella, F., et al., "Endothelin-1 Induces Vascular Endothelial Growth Factor by Increasing Hypoxia-inducible Factor-1α in Ovarian Carcinoma Cells", Journal of Biological Chemistry, vol. 31, pp. 27850-27855, (2002).

Thaker, P.H., et al., "Antivascular Therapy for Orthotopic Human Ovarian Carcinoma through Blockade of the Vascular Endothelial Growth Factor and Epidermal Growth Factor Receptors", Clinical Cancer Research, vol. 11(13), pp. 4923-4933, (2005).

Witteveen, P.O., et al., "A phase I study of atrasentan in combination with liposomal doxorubicin in platinum resistant ovarian cancer", Journal of Clinical Oncology, 2005 ASCO Annual Meeting Proceedings, vol. 23, No. 16S, p. 3170, (2005).

Godara, Geeta, et al., "Role of Endothelin Axis in Progression to Aggressive Phenotype of Prostate Adenocarcinoma" Prostate, vol. 65, No. 1, Sep. 1, 2005, pp. 27-34, XP002527395 (abstract).

Iglarz, Marc, et al., "Pharmacology of Macitentan, an Orally Active Tissue-Targeting Dual Endothelin Receptor Antagonist", The Journal of Pharmacology and Experimental Therapeutics, vol. 327, No. 3, pp. 736-745, (2008).

Salani, Debora, et al., "ABT-627, A Potent Endothelin Receptor A Antagonist, Inhibits Ovarian Carcinoma Growth In Vitro", The Biochemical Society and the Medical Research Society, (2002).

Office Action—Restriction from the USPTO for U.S. Appl. No. 12/439,290 dated Jun. 1, 2011 and Response thereto dated Jul. 1, 2011.

Office Action—Non-Final from the USPTO for U.S. Appl. No. 12/439,290 dated Sep. 27, 2011 and Response thereto dated Dec. 27, 2011.

Office Action—Final from the USPTO for U.S. Appl. No. 12/439,290 dated Feb. 28, 2011 and Response thereto dated Apr. 27, 2012.

Notice of Allowance from the USPTO for U.S. Appl. No. 12/439,290 dated May 21, 2012.

Notice of Allowance from the USPTO for U.S. Appl. No. 12/388,142 dated Sep. 25, 2012.

Response to Office Action dated Aug. 31, 2012 for EP Application No. 09712334.3.

Buckanovich et al., "Endothelin B Receptor Mediates the Endothelial Barrier to T Cell Homing to Tumors and Disables Immune Therapy", Nature Medicine, vol. 14, No. 1, p. 28-36 (Jan. 2008).

Kim et al., "Macitentan (ACT-064992), A Tissue-Targeting Endothelin Receptor Antagonist, Enhances Therapeutic Efficacy of Paclitaxel by Modulating Survival Pathways in Orthotopic Models of Metastatic Human Ovarian Cancer", Neoplasia, vol. 13, No. 2, pp. 167-179 (Feb. 2011).

Kim et al., "Antivascular Therapy for Multidrug-Resistant Ovarian Tumors by Macitentan, A Dual Endothelin Receptor Antagonist", Translational Oncology, vol. 5, No. 1, pp. 39-47 (Feb. 2012).

* cited by examiner

COMBINATION COMPRISING MACITENTAN AND PACLITAXEL FOR TREATING MULTI-DRUG RESISTANT OVARIAN CANCER

CROSS REFEREBCE TO RELATED APPLICATIONS

This application is a United States Application filed under 35 U.S.C.§371 claiming benefit to PCT Application No. PCT/IB2009/050677, filed on Feb. 19, 2009, which claims the benefit of PCT Application No. PCT/IB2008/050607, filed on Feb. 20, 2008.

The present invention concerns the combination of an endothelin receptor antagonist of formula (I)

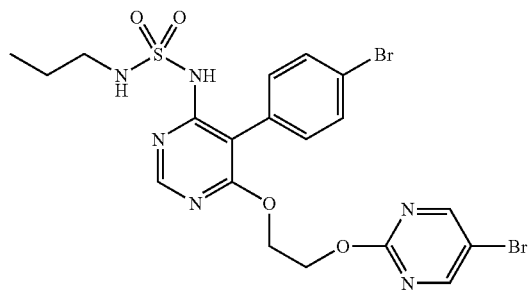

(I)

with paclitaxel for therapeutic use, simultaneously, separately or over a period of time, in the treatment of ovarian cancer.

Ovarian cancer is one of the most common cancers in women. A common complication of ovarian cancer is ascite formation. Today, there is no satisfactory treatment for ovarian cancer or for its complications such as ascite formation.

PCT publication WO 02/053557 describes endothelin receptor antagonists including the compound of formula (I) (the International Nonproprietary Name of which is macitentan) and the use of said endothelin receptor antagonists in the treatment of various diseases, including cancer in general.

Paclitaxel (the active principle of a medicament sold under the trademark Taxol® in the United States) is an anti-microtubule agent extracted from the needles and bark of the Pacific yew tree, *Taxus brevifolia*. This compound is currently approved in the European Union and the United States for, among others, the treatment of advanced cancer of the ovary.

The combination of endothelin receptor A ($ET_AR$) antagonists with paclitaxel in the treatment of ovarian cancer has already been suggested in literature.

For example, L. Rosano et al (*Cancer Res.* (2003), 63, 2447-2453) teach that the selective $ET_AR$ antagonist ABT-627 (atrasentan) combined with paclitaxel produced additive antitumor, apoptotic and antiangiogenic effects.

Besides, L. Rosano et al (*Mol. Cancer Ther.* (2007), 6(7), 2003-2011) disclosed that ZD4054, a specific $ET_AR$ antagonist, inhibits tumor growth and enhances paclitaxel activity in human ovarian carcinoma in vitro and in vivo.

On the other hand, L. Rosano et al (*Mol. Cancer Ther.* (2006), 5(4), 833-842) also showed that BQ 788, a selective endothelin receptor B ($ET_BR$) antagonist, contrarily to $ET_AR$ antagonists, was ineffective in inhibiting cell adhesiveness of ovarian tumor cells in vitro.

The applicant has now found that the compound of formula (I), which is both an $ET_AR$ and an $ET_BR$ antagonist, produces surprisingly high effects in several in vivo models of ovarian cancer when combined with paclitaxel. Besides, in one of these in vivo models, the applicant found that the use of the combination of the compound of formula (I) with paclitaxel prevents or treats the formation of ascites. As a result, the compound of formula (I) in combination with paclitaxel may be used for the preparation of a medicament, and is suitable, for the treatment of ovarian cancer and/or the prevention or treatment of ascite formation associated with ovarian cancer.

The invention thus firstly relates to a product containing the compound of formula (I) below

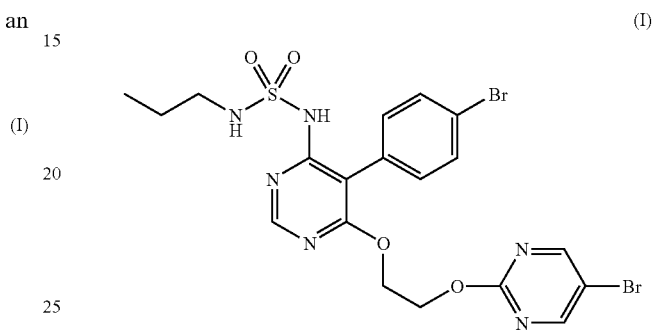

(I)

or a pharmaceutically acceptable salt of this compound, in combination with paclitaxel, or a pharmaceutically acceptable salt thereof, as well as to said product for therapeutic use, simultaneously, separately or over a period of time, in the treatment of ovarian cancer.

The following paragraphs provide definitions of the various terms used in the present patent application and are intended to apply uniformly throughout the specification and claims, unless an otherwise expressly set out definition provides a broader or narrower definition.

The term "pharmaceutically acceptable salt" refers to non-toxic, inorganic or organic acid and/or base addition salts. Reference can be made to "Salt selection for basic drugs", *Int. J. Pharm.* (1986), 33, 201-217.

"Simultaneously" or "simultaneous", when referring to a therapeutic use, means in the present application that the therapeutic use concerned consists in the administration of two or more active ingredients by the same route and at the same time.

"Separately" or "separate", when referring to a therapeutic use, means in the present application that the therapeutic use concerned consists in the administration of two or more active ingredients at approximately the same time by at least two different routes.

By therapeutic administration "over a period of time" is meant in the present application the administration of two or more ingredients at different times, and in particular an administration method according to which the entire administration of one of the active ingredients is completed before the administration of the other or others begins. In this way it is possible to administer one of the active ingredients for several months before administering the other active ingredient or ingredients. In this case, no simultaneous administration occurs. Therapeutic administration "over a period of time" also encompasses situations wherein the ingredients are not given with the same periodicity (e.g. wherein one ingredient is given once a day and another is given once a week).

By "prevention of ascite formation" or "preventing ascite formation" is meant in the present application that, following the administration of the appropriate preventive treatment according to this invention, the formation of ascites is either avoided or that this formation is reduced, or, alternatively, that the ascites nevertheless formed are eliminated or reduced.

By "treatment of ascite formation" or "treating ascite formation" is meant in the present application that, following the administration of the appropriate treatment according to this invention, the ascites present in the patient are eliminated or reduced.

In a preferred embodiment of this invention, the product containing the abovementioned compound of formula (I) or a pharmaceutically acceptable salt of this compound, in combination with paclitaxel, or a pharmaceutically acceptable salt thereof, will be for therapeutic use, simultaneously, separately or over a period of time, in the prevention or treatment of ascite formation in patients having ovarian cancer.

According to one variant of this invention, the compound of formula (I) or its pharmaceutically acceptable salt will be intended to be administered by intravenous or intraperitoneal route.

According to another variant of this invention, the compound of formula (I) or its pharmaceutically acceptable salt will be intended to be administered by oral route.

Paclitaxel or its pharmaceutically acceptable salt will preferably be administered by intravenous or intraperitoneal route.

Though the exact administration doses of a product according to this invention will have to be determined by the treating physician, it is expected that a dose of 0.01 to 10 mg (and preferably 0.1 to 5 mg and more preferably 0.1 to 1 mg) of compound of formula (I) per kg of patient body weight per day combined with a dose of 0.1 to 10 mg (and preferably 1 to 3 mg) of paclitaxel per kg of patient body weight per day, will be appropriate.

The invention also relates to a pharmaceutical composition containing, as active principles, the compound of formula (I) as defined previously, or a pharmaceutically acceptable salt of this compound, in combination with paclitaxel, or a pharmaceutically acceptable salt thereof, as well as at least one non-toxic excipient.

Preferably, such a pharmaceutical composition will be in a liquid form suitable for intravenous or intraperitoneal administration. In particular, said pharmaceutical composition may contain the compound of formula (I) or a pharmaceutically acceptable salt of this compound and paclitaxel or a pharmaceutically acceptable salt thereof, in solution in a mixture of polyoxyethylated castor oil (e.g. Cremophor® EL) and ethanol (said mixture containing for example from 40 to 60% in volume of polyoxyethylated castor oil in ethanol).

Alternatively, the compound of formula (I) may be formulated as a tablet as described in WO 2007/031933, whereas paclitaxel may be formulated as a solution in a mixture of polyoxyethylated castor oil (e.g. Cremophor® EL) and ethanol.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The invention further relates to the use of the compound of formula (I) as defined previously, or a pharmaceutically acceptable salt of this compound, in combination with paclitaxel, or a pharmaceutically acceptable salt thereof, for the manufacture of a medicament intended to treat ovarian cancer. It also relates to the use of the compound of formula (I) as defined previously, or a pharmaceutically acceptable salt of this compound, in combination with paclitaxel, or a pharmaceutically acceptable salt thereof, for the manufacture of a medicament intended to prevent or treat ascite formation in patients having ovarian cancer.

The invention further relates to a method of treating a patient having an ovarian cancer by administering to said patient a combination of the compound of formula (I) as defined previously or a pharmaceutically acceptable salt of this compound, with paclitaxel or a pharmaceutically acceptable salt thereof. It also relates to a method of preventing or treating the formation of ascites in a patient having an ovarian cancer by administering to said patient a combination of the compound of formula (I) as defined previously or a pharmaceutically acceptable salt of this compound, with paclitaxel or a pharmaceutically acceptable salt thereof.

Besides, preferences indicated for the product according to this invention of course apply mutatis mutandis to the pharmaceutical compositions and uses of this invention.

Particular embodiments of the invention are described in the following section, which serves to illustrate the invention in more detail without limiting its scope in any way.

PHARMALOGICAL PROPERTIES OF THE INVENTION PRODUCT

Human SKOV3ip1 Tumor Growth Inhibition Assay in Mice

Experimental Methods:

Vehicle Solution

An aqueous 0.5% (by weight) solution of methylcellulose is prepared by stirring the appropriate quantity of methylcellulose in the appropriate quantity of water for 4 hours. This solution can be prepared up to 3 days in advance. On the day of the experiment, 0.05% (by volume) of Tween 80 is dissolved in the methylcellulose solution previously obtained to yield the vehicle solution.

Experimental Procedure 43 mice are injected i.p. with $10^6$ SKOV3ip1 cells. Ten days later, the tumor weight is evaluated in three of the mice. Treatment with a suspension of the compound of formula (I) in the vehicle solution (10 mice), paclitaxel (Mead Johnson, Princeton, N.J., USA) diluted 1:6 in phosphate buffered saline (PBS) for i.p. injections (10 mice), a suspension of the compound of formula (I) in the vehicle solution as well as paclitaxel diluted 1:6 in PBS for further dilution and i.p. injections (10 mice), or the vehicle solution only (10 mice), the vehicle solution being as described above, is administered to the mice using the following doses, frequencies and routes:

paclitaxel: 5 mg/kg (125 µg paclitaxel in 200 µL PBS per mouse), once a week, i.p. route;

compound of formula (I): 100 mg/kg (as suspension in the vehicle solution at a concentration of up to 25 mg/mL), once a day, oral route.

After one month of treatment, the tumor incidence and weight are determined in each of the mice. At the same time, the ascite incidence and volume are also determined.

Results:

The following results were obtained with respect to tumor incidence and weight:

| Treatment group | Body weight (g) Mean ± S.D. | Tumor incidence | Tumor weight (g) Median (range) | p |
|---|---|---|---|---|
| Control | 23.1 ± 2.5 | 8/10 | 1.1 (0-1.8) | |
| Paclitaxel | 23.6 ± 1.9 | 9/9 | 0.4 (0.1-0.5) | 0.01 |
| CF(I) | 25.5 ± 2.6 | 7/10 | 2.3 (0-4.6) | 0.08 |
| Paclitaxel + CF(I) | 23.3 ± 2.3 | 5/9 | 0.1 (0-0.3) | 0.001 |

S.D. = standard deviation CF(I) = compound of formula (I)

The following results were obtained with respect to ascite incidence and volume:

| Treatment group | Body weight (g) Mean ± S.D. | Ascite incidence | Ascites (mL) Median (range) | p |
|---|---|---|---|---|
| Control | 23.1 ± 2.5 | 8/10 | 0.4 (0-0.9) | |
| Paclitaxel | 23.6 ± 1.9 | 4/9 | 0.1 (0-0.2) | 0.005 |
| CF(I) | 25.5 ± 2.6 | 7/10 | 0.4 (0-4.7) | 0.27 |
| Paclitaxel + CF(I) | 23.3 ± 2.3 | 0/9 | 0 | 0.002 |

S.D. = standard deviation CF(I) = compound of formula (I)

As can be seen, the combination of the compound of formula (I) with paclitaxel markedly increased the response to the paclitaxel treatment alone:

- four out of nine mice were tumor-free after the combination treatment while all mice still had tumors in the paclitaxel-treated group;
- the tumor was on average four times bigger in the paclitaxel-treated group than in the combination treated group; and
- no mouse treated with the combination developed ascites even though 5 out of 9 still had tumors, whereas ascites were present in 4 out of 9 mice treated with paclitaxel alone and in 7 out of 10 mice treated with the compound of formula (I) alone.

Human IGROV Tumor Growth Inhibition Assay in Mice

Experimental Methods:

Vehicle Solution

The vehicle solution is the same as that described for the "Human SKOV3ip1 tumor growth inhibition assay in mice" (see above).

Experimental Procedure 43 female nude mice are injected i.p. with $10^6$ IGROV cells into the peritoneal cavity. Ten days later, the tumor weight is evaluated in three of the mice. Treatment with a suspension of the compound of formula (I) in the vehicle solution (10 mice), paclitaxel diluted 1:6 in phosphate buffered saline (PBS) for i.p. injections (10 mice), a suspension of the compound of formula (I) in the vehicle solution as well as paclitaxel diluted 1:6 in PBS for i.p. injections (10 mice), or the vehicle solution only (10 mice), the vehicle solution being as described above, is administered to the mice using the following doses, frequencies and routes:

- paclitaxel: 5 mg/kg (125 μg paclitaxel in 200 μL PBS per mouse), once a week, i.p. route;
- compound of formula (I): 50 mg/kg (as suspension in the vehicle solution at a concentration of up to 25 mg/mL), once a day, oral route.

After 4 weeks of treatment, the tumor incidence and weight are determined in each of the mice.

Results:

The following results were obtained with respect to tumor incidence and weight:

| Treatment group | Body weight (g) Mean ± S.D. | Tumor incidence | Tumor weight (g) Median (range) | p |
|---|---|---|---|---|
| Control | 28.0 ± 3.2 | 10/10 | 1.1 (0.4-2.1) | |
| Paclitaxel | 28.5 ± 2.4 | 9/10 | 0.5 (0-0.9) | 0.057 |
| CF(I) | 31.0 ± 4.4 | 10/10 | 0.7 (0.4-1.3) | 0.195 |
| Paclitaxel + CF(I) | 29.4 ± 6.1 | 9/10 | 0.3 (0-0.6) | 0.0006 |

S.D. = standard deviation CF(I) = compound of formula (I)

As can be seen, the maximal tumor size reduction was achieved in the human IGROV tumor model in mice using the combination of the compound of formula (I) with paclitaxel.

Multi-Drug Resistant Human Ovarian HeyA8-MDR Tumor Growth Inhibition Assay in Mice Experimental Methods:

Vehicle Solution

The vehicle solution is the same as that described for the "Human SKOV3ip1 tumor growth inhibition assay in mice" (see above).

Experimental Procedure 43 female nude mice are injected i.p. with $10^6$ HeyA8-MDR cells into the peritoneal cavity. Ten days later, the tumor weight is evaluated in three of the mice. Mice groups and treatments (doses, frequencies and routes) for the mice groups are the same as those described in the experimental procedure for the "Human IGROV tumor growth inhibition assay in mice" (see above). After 4 weeks of treatment, the tumor incidence and weight are determined in each of the mice.

Results:

The following results were obtained with respect to tumor incidence and weight:

| Treatment group | Body weight (g) Mean ± S.D. | Tumor incidence | Tumor weight (g) Median (range) | p |
|---|---|---|---|---|
| Control | 28.5 ± 2.8 | 10/10 | 1.1 (0.1-3.2) | |
| Paclitaxel | 27.7 ± 3.7 | 10/10 | 1.0 (0.5-2.3) | 0.52 |
| CF(I) | 27.0 ± 2.2 | 6/10 | 0.1 (0-0.3) | 0.004 |
| Paclitaxel + CF(I) | 27.0 ± 3.0 | 5/10 | 0.025 (0-0.7) | 0.0005 |

S.D. = standard deviation CF(I) = compound of formula (I)

As can be seen, the maximal tumor size reduction was achieved in the multi-drug resistant human ovarian HeyA8-MDR tumor model in mice using the combination of the compound of formula (I) with paclitaxel. Using this combination, half of the mice treated were tumor-free at the end of the treatment.

The invention claimed is:

1. A. method for the treatment of multi-drug resistant ovarian cancer, comprising administering, simultaneously, separately or over a period of time, to a patient in need thereof, a compound of formula (I):

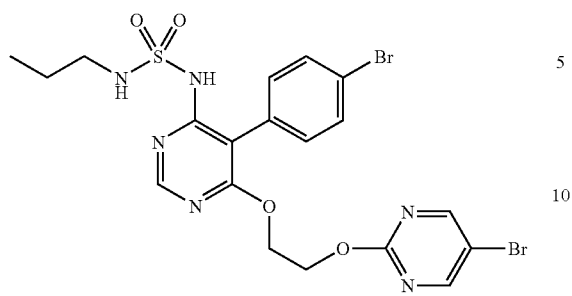 (I)

in free or pharmaceutically acceptable salt form, in combination with paclitaxel, in free or pharmaceutically acceptable salt form.

2. The method according to claim 1, wherein the compound of formula (I) in free or pharmaceutically acceptable salt form is administered by intravenous or intraperitoneal route.

3. The method according to claim 1, wherein the compound of formula (I) in free or pharmaceutically acceptable salt form is administered by oral route.

4. The method according to claim 1, wherein paclitaxel in free or pharmaceutically acceptable salt form is administered by intravenous or intraperitoneal route.

* * * * *

UNITED STATES PATENT AND TRADEMARK OFFICE
CERTIFICATE OF CORRECTION

PATENT NO. : 8,541,433 B2  Page 1 of 1
APPLICATION NO. : 12/867939
DATED : September 24, 2013
INVENTOR(S) : Clozel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this
Eighth Day of March, 2016

Michelle K. Lee
*Director of the United States Patent and Trademark Office*